US007018353B2

(12) United States Patent
Hunley et al.

(10) Patent No.: US 7,018,353 B2
(45) Date of Patent: Mar. 28, 2006

(54) HEMATOCRIT SAMPLING SYSTEM

(75) Inventors: Steven Kenneth Hunley, Loveland, CO (US); Rainer Harald Koenig, Denver, CO (US)

(73) Assignee: COBE Cardiovascular, Inc., Arvada, CO (US)

( * ) Notice: Subject to any disclaimer, the term of this patent is extended or adjusted under 35 U.S.C. 154(b) by 88 days.

(21) Appl. No.: 10/408,894

(22) Filed: Apr. 8, 2003

(65) Prior Publication Data

US 2003/0195452 A1 Oct. 16, 2003

Related U.S. Application Data

(63) Continuation of application No. 09/587,122, filed on Jun. 2, 2000, now Pat. No. 6,554,788.

(51) Int. Cl.
*A61M 37/00* (2006.01)
*B01D 11/00* (2006.01)
*B01D 35/00* (2006.01)
*B01D 21/26* (2006.01)
*C02F 1/52* (2006.01)

(52) U.S. Cl. .................. 604/4.01; 604/6.01; 604/6.16; 210/645; 210/85; 210/739; 600/312; 494/37

(58) Field of Classification Search .............. 604/4.01, 604/5.01, 6.01, 6.08, 6.16; 600/300, 320, 600/322–23, 310, 326–8, 334, 368, 370; 210/645, 650, 745, 740, 781–82, 739, 86–9, 210/90, 85, 138–143; 436/66, 70; 435/2
See application file for complete search history.

(56) References Cited

U.S. PATENT DOCUMENTS

| | | | |
|---|---|---|---|
| 4,227,814 A | 10/1980 | Soodak et al. | |
| 4,243,883 A | 1/1981 | Schwarzmann | |
| 4,266,021 A | 5/1981 | Nylen et al. | |
| 4,484,135 A | 11/1984 | Ishihara et al. | |
| 4,745,279 A | 5/1988 | Karkar et al. | |
| 5,104,623 A | 4/1992 | Miller | |
| 5,331,958 A | 7/1994 | Oppenheimer | |
| 5,351,686 A | 10/1994 | Steuer et al. | |
| 5,385,539 A | 1/1995 | Maynard | |
| 5,423,738 A | 6/1995 | Robinson et al. | |
| 5,456,253 A * | 10/1995 | Steuer et al. ............... | 600/322 |
| 5,681,273 A * | 10/1997 | Brown ....................... | 604/6.07 |
| 5,976,388 A | 11/1999 | Carson | |
| 6,080,322 A | 6/2000 | Deniega et al. | |

OTHER PUBLICATIONS

International Search Report for counterpart PCT application, PCT/US01/17680 (4 pages).

* cited by examiner

*Primary Examiner*—Patricia Bianco
(74) *Attorney, Agent, or Firm*—Popovich, Wiles & O'Connell, P.A.

(57) ABSTRACT

Accurate measurement of hematocrit during blood recovery or plasma sequestration processes by means of algorithms to account for the presence of air or other non-blood substances in salvaged or separated blood is described. A method of automatic start-up of the hematocrit measurement circuit and a method of determining the minimum volume of blood required to obtain an accurate measurement of the hematocrit also is described.

14 Claims, 5 Drawing Sheets

HEMATOCRIT SAMPLING SYSTEM

This application is a continuation of Ser. No. 09/587,122 filed Jun. 6, 2000, now U.S. Pat. No. 6,554,788.

FIELD OF THE INVENTION

The present invention relates to extracorporeal blood processing. More particularly, this invention relates to a method and apparatus for the automated sampling of the hematocrit of blood.

BACKGROUND OF THE INVENTION

The collection and reinfusion of a patient's own blood, referred to as autologous blood, offers a number of recognized benefits. For example, the use of autologous blood reduces concerns relating to the possibility of disease transmission via donor blood transfusions, referred to as homologous blood, as well as concerns regarding febrile/allergic reactions. Additionally, autologous blood recovery ensures the rapid availability of blood and reduces or eliminates the need for compatibility testing on such blood since the procedure is most typically completed in an operating room. Further, the use of autologous blood provides red blood cells which are generally superior in quality to banked blood and reduces any quantity of homologous blood otherwise needed. The use of autologous blood is also desirous to many patients for psychological and/or religious reasons.

Intraoperative procedures where autologous blood salvage is currently employed include cardiac and vascular surgery. Specialties which employ autologous blood salvage include orthopedics, plastic and reconstructive surgery, neurosurgery, solid organ transplants, general surgery, gynecology and trauma.

In a typical blood salvage procedure, blood is removed from or about a surgical site via a hand-held suction device, mixed with an anticoagulant, and transferred to a reservoir for subsequent transfer for batch processing. In connection with such collection/transfer of salvaged blood, the blood is typically filtered to remove debris and defoamed to remove entrained gaseous components (e.g. air) utilizing separate in-line filter devices and defoaming devices through which the salvaged blood is sequentially transferred. During batch processing, the salvaged blood and a wash solution are separately pumped in sequence through a centrifuge to separate red blood cells and achieve a degree of washing. Following processing, the red blood cells are removed from the centrifuge for reinfusion to the patient.

Another blood processing procedure is apheresis. Apheresis is a procedure of separating the blood into its various components via centrifugation. By appropriate adjustment of the separation instrument, a selected portion of the blood can be recovered while the rest of the blood is returned to the donor. Examples include plasmapheresis, plateletpheresis and red blood cell collection.

Plasma sequestration is a procedure which may include both plasmapheresis and plateletpheresis. Plasmapheresis is a process whereby plasma containing few cellular components (i.e., platelet poor plasma) is collected. Plateletpheresis is a process whereby plasma containing many cellular components (i.e., platelet rich plasma) is collected. This process also commonly uses centrifugation as its separation mechanism. The plasma component as well as the cellular components may be returned to the patient at the appropriate time.

In blood salvage and red cell collection procedures the objective is to obtain a high quality and amount of red blood cells in the least amount of overdue procedure time. A way to monitor the quality of the procedure is by measuring the hematocrit of the processed blood and maintaining it in a desired range. Methods of doing this include those disclosed in U.S. Pat. No. 5,385,539 (Maynard), which describes a hematocrit sensor used in a plasma separator apparatus. The hematocrit sensor continuously monitors the hematocrit level of processed blood, and adjusts the parameters of the plasma separator apparatus to compensate for a hematocrit that is too high or too low. However, many problems remain in this area, including, for example, variability in the measured hematocrit due to loss of hematocrit sampling data caused by non-blood substances such as air bubbles, or other obstructions in the blood flow path (e.g. clots, fat, etc.) that interfere with the detector signal. In addition, operator error remains a problem with such blood separation and measurement/analysis systems.

SUMMARY OF THE INVENTION

This invention provides for accurate measurement of hematocrit during blood recovery or plasma sequestration processes by means of algorithms to account for the presence of air or other non-blood substances in salvaged or separated blood. This invention also provides a method of automatic start-up of the hematocrit measurement circuit. Further, this invention is a method of determining the minimum volume of blood required to obtain an accurate measurement of the hematocrit.

In one aspect, this invention is a method of determining the average hematocrit of blood processed in a blood processing system, comprising providing a blood processing system having a blood inlet and a blood outlet, the blood processing system being sized to process a known volume of blood during a processing cycle; providing a hematocrit measurement circuit connected to measure the hematocrit of blood flowing through the outlet of the blood processing system, the hematocrit measurement circuit having a display for reporting hematocrit values; determining a minimum volume of the known volume of blood which must be measured for hematocrit in order for an average hematocrit value for the known volume of blood to be calculated within a predetermined degree of accuracy; evacuating processed blood from the system through the blood outlet; making a plurality of hematocrit measurements of the processed blood; calculating from the plurality of hematocrit measurements an average hematocrit value for a first volume of processed blood; and comparing the first volume to the minimum volume.

The method may further include reporting the average hematocrit of the known volume of processed blood if the first volume is at least as great as the minimum volume.

In another aspect, this invention is a method of measuring hematocrit in processed blood comprising providing a blood processing system having a blood inlet and a blood outlet, the blood processing system being sized to process a known volume of blood during each processing cycle; providing a hematocrit measurement circuit having a hematocrit sensor connected to measure the hematocrit of blood flowing through the outlet of the blood processing system, the hematocrit measurement circuit having a known lock time after which the circuit first responds to the presence of blood sensed by the sensor; evacuating processed blood from the system through the blood outlet; making a plurality of hematocrit measurements of the processed blood; assigning a hematocrit value to a first volume of processed blood passing the hematocrit sensor during the lock time; and calculating from the plurality of hematocrit measurements and assigned hematocrit value an average hematocrit value of the known volume of processed blood evacuated from the system.

The assigning step may comprise using an algorithm that calculates the hematocrit value based on at least one of the plurality of hematocrit measurements. The step of using the algorithm to calculate the hematocrit value comprises assigning to the first volume of processed blood a hematocrit value equal to the first processed blood hematocrit measurement after the lock time. The step of using the algorithm to calculate the hematocrit value may comprise determining a slope of the first N processed blood hematocrit measurements after the lock time and extrapolating backwards using the slope to assign a hematocrit value to the first volume of processed blood.

The method further includes determining the presence of non-blood substances in the processed blood from the plurality of hematocrit measurements and assigning a hematocrit value to a second volume of processed blood, the second volume being determined from hematocrit measurements of non-blood substances in the processed blood. The step of assigning a hematocrit value to the second volume of processed blood comprises using an algorithm that calculates the hematocrit value based on at least one of the plurality of hematocrit measurements. The step of using an algorithm to calculate a hematocrit value for the second volume of processed blood may comprise assigning to the second volume of processed blood a hematocrit value equal to the average of the last processed blood hematocrit measurement prior to the non-blood substance and the first processed blood hematocrit measurement after the non-blood substance.

In a third aspect, this invention is a method of measuring hematocrit in processed blood comprising providing a blood processing system having a blood inlet and a blood outlet; providing a hematocrit measurement circuit connected to measure the hematocrit of blood flowing through the outlet of the blood processing system; evacuating processed blood from the system through the blood outlet; making a plurality of hematocrit measurements; determining the presence of non-blood substances in the processed blood from the hematocrit measurements; assigning a hematocrit value to a volume of processed blood based on hematocrit measurements of non-blood substances in the processed blood; and calculating from the measured hematocrit and assigned hematocrit values an average hematocrit value of process blood evacuated from the system.

The hematocrit measurement circuit may include a hematocrit sensor connected to measure the hematocrit of blood flowing through the outlet of the blood processing system and wherein the hematocrit measurement system has a known lock time after which the circuit first responds to the presence of blood sensed by the sensor, the method further including assigning a hematocrit value to a second volume of processed blood passing the hematocrit sensor during the lock time.

In a fourth aspect, this invention is a blood processing system comprising a blood processor having an inlet and an outlet, the blood processor being sized to process a known volume of blood during a processing cycle; a hematocrit sensor connected to measure hematocrit of process blood flowing through the outlet of the blood processor at a predetermined sampling rate, the sensor being configured to provide data indicative of the hematocrit of the process blood being sensed and to provide data indicative of non-blood substances when substances other than blood are being sensed; and a controller connected to receive the data from the sensor and to calculate from the data an average hematocrit value of the known volume of processed blood, the calculation being performed in a manner that makes adjustments to the calculation depending on the presence of non-blood substances in the processed blood.

In a fifth aspect, this invention is a blood processing system comprising a blood processor having an inlet and an outlet; a hematocrit sensing circuit including a hematocrit sensor configured to connect with a first connector when the blood processor is not in use and with a second connector when the blood processor is in use, the second connector being connected to the outlet of the blood processor, the hematocrit sensing circuit being switchable from an operational mode when the sensor is making hematocrit measurements and a non-operational mode when the sensor is not making hematocrit measurements, the hematocrit sensing circuit being further configured to be switched to the operational mode when the sensor is disconnected from the first connector.

In a sixth aspect, this invention is a blood processing system comprising a blood processor having an inlet and an outlet; a hematocrit sensing circuit including a hematocrit sensor configured to connect with a first connector when the blood processor is not in use and with a second connector when the blood processor is in use, the second connector begin connected to the outlet of the blood processor, the hematocrit sensing circuit being switchable from an operational mode when the sensor is making hematocrit measurements and a non-operational mode when the sensor is not making hematocrit measurements, the hematocrit sensing circuit being further configured to be switched to the operational mode when the sensor is connected to the second connector.

DETAILED DESCRIPTION OF PREFERRED EMBODIMENTS

This invention provides for accurate measurement of hematocrit during blood recovery or plasma sequestration processes by means of algorithms to account for the presence of air or other non-blood substances in salvaged or separated blood. Blood recovery processes include autologous blood salvage and apheresis procedures including plateletpheresis and plasmapheresis (i.e. plasma sequestration). Commercially available autologous blood salvage systems include, for example, the BRAT 2® intraoperative blood recovery system, available from Cobe Cardiovascular, Inc. of Denver, Colo. U.S. Pat. No. 5,979,388 (Carson) also describes a method and apparatus for autologous blood salvage, and is hereby incorporated herein by reference. The hematocrit measurement system may also be used with other autotransfusion systems, such as a plasma separator apparatus, as is known in the art.

Measurement of Hematocrit

Figure 1:
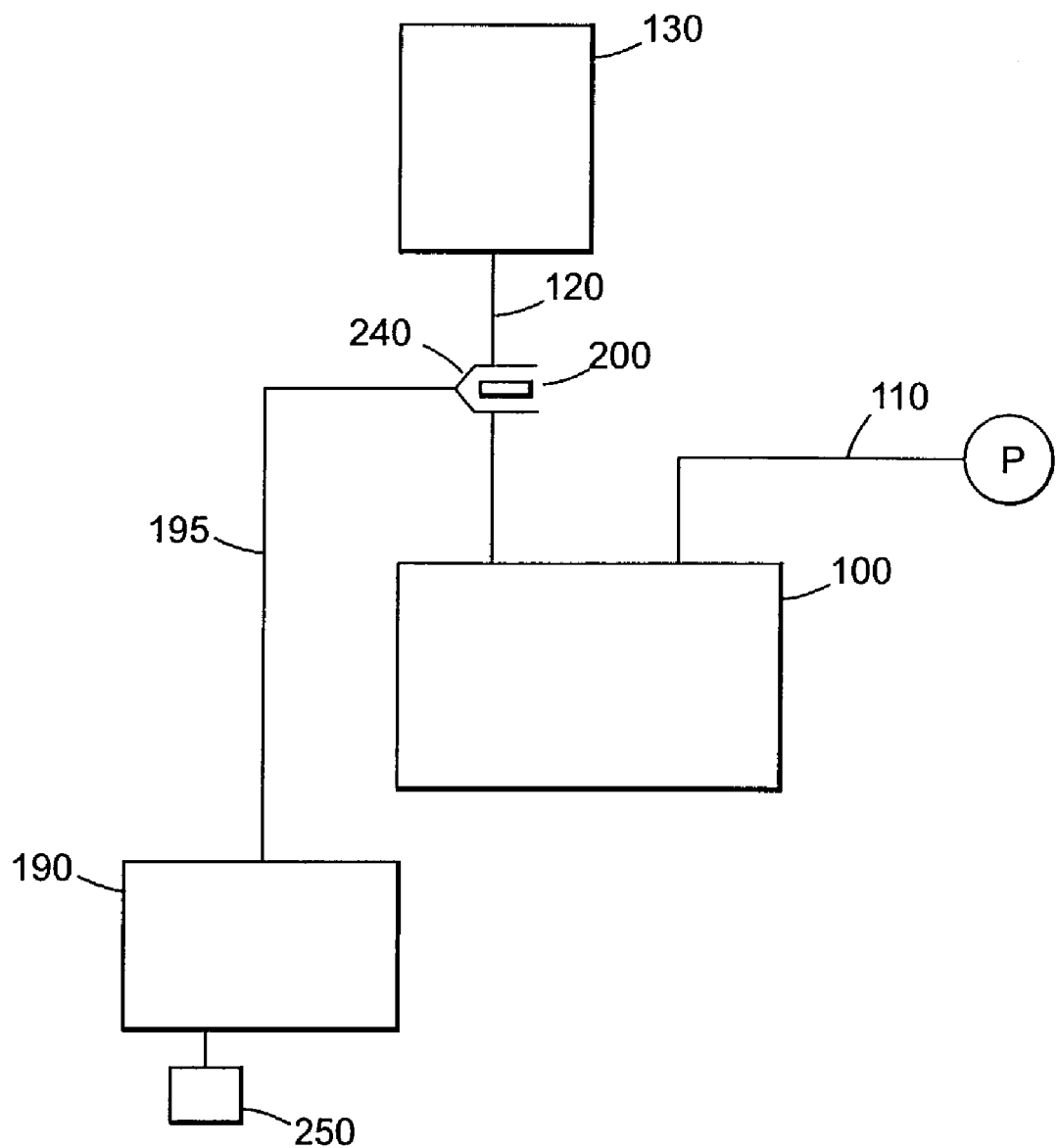
FIG. 1 is a schematic illustration of a blood recovery system of the present invention.

FIG. 1 illustrates a blood recovery system, such as autologous blood salvage or plasma separation, provided with a hematocrit measurement circuit that enables the hematocrit of the processed blood at the outlet of the system to be measured in several modes. Specifically, the hematocrit measuring circuit will provide: (1) an instantaneous reading of hematocrit in processed blood passing by the sensor, (2) the hematocrit of blood processed in individual containment bowls, and (3) the hematocrit of blood processed during a procedure which includes multiple containment bowls.

Blood recovery system 100 may comprise various storage and separation assemblies and one or more pumps to suction blood from the patient P into system 100 via fluid line 110. The recovery system may include a centrifuge which permits the separation of blood components. Such a system may include, for example, a centrifuge bowl as described in U.S. Pat. No. 5,919,125 (Berch), hereby incorporated herein by reference. Processed blood flows out of blood recovery system 100 through outlet line 120 through a hematocrit sampling circuit, described further below and into reinfusion bag 130. The hematocrit sampling circuit permits the evaluation of blood quality before its return to the patient.

Figure 2A:
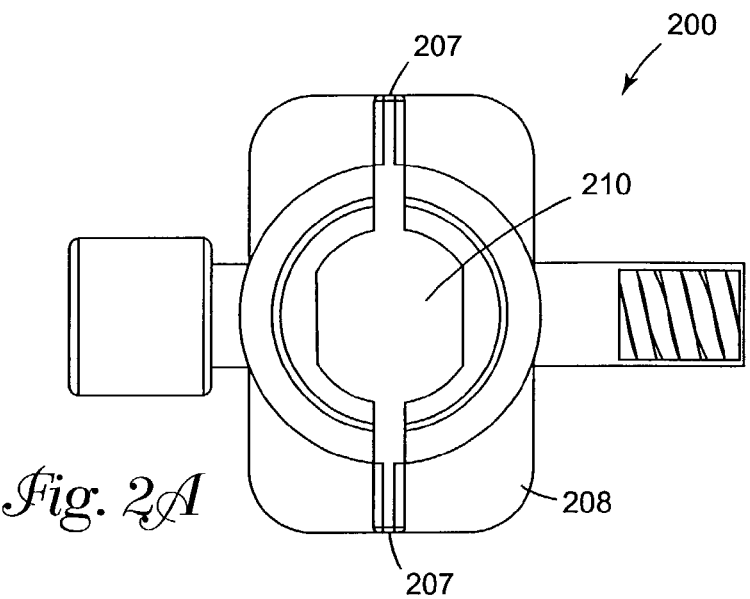
FIG. 2A illustrates a back sectional view of the blood sampling cuvette used with the blood recovery system shown in FIG. 1.
Figure 2B:
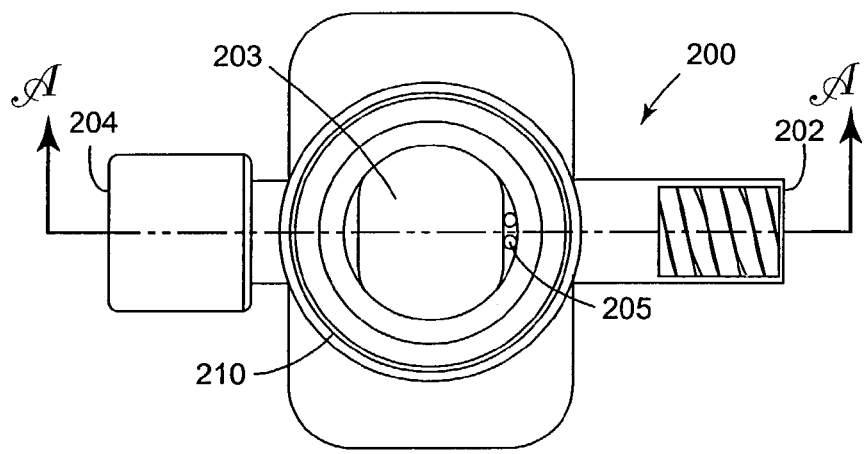
FIG. 2B illustrates a front sectional view of the cuvette.
Figure 2C:
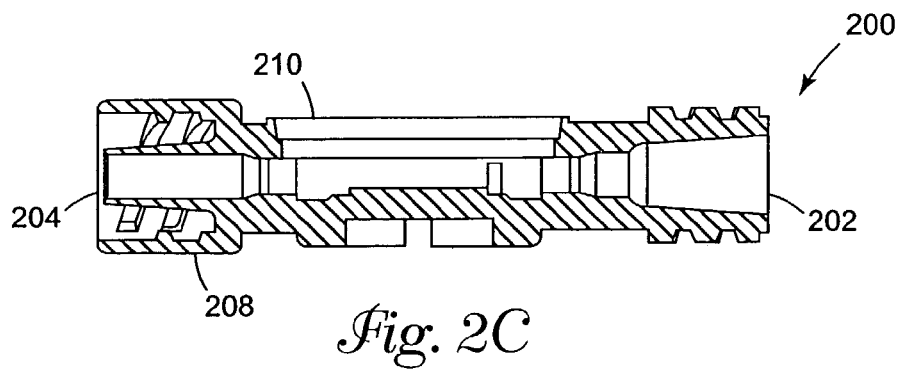
FIG. 2C illustrates a sectional view of the cuvette taken along line A—A of FIG. 2B.
Figure 3A:
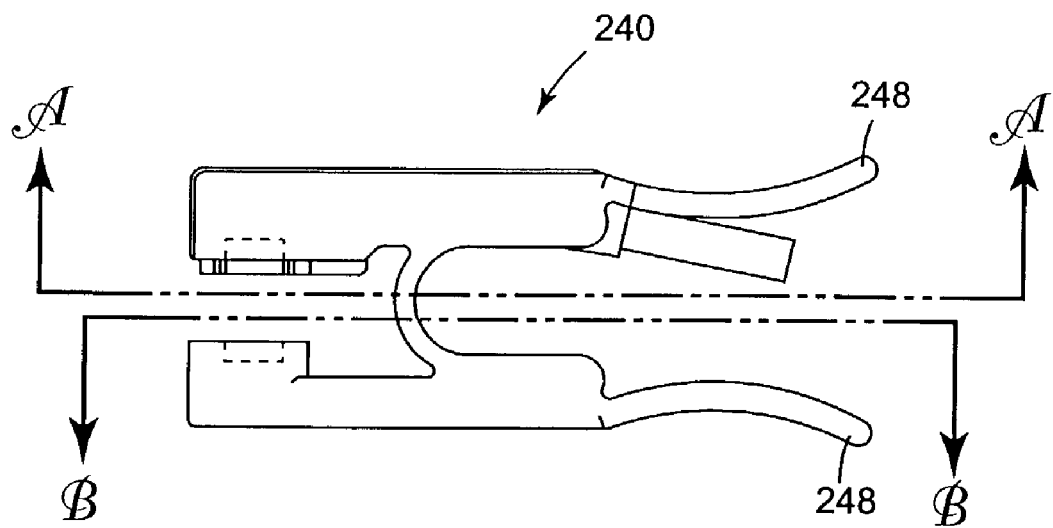
FIG. 3A illustrates a sectional view of the hematocrit detector used with the blood recovery system shown in FIG. 1.
Figure 3B:
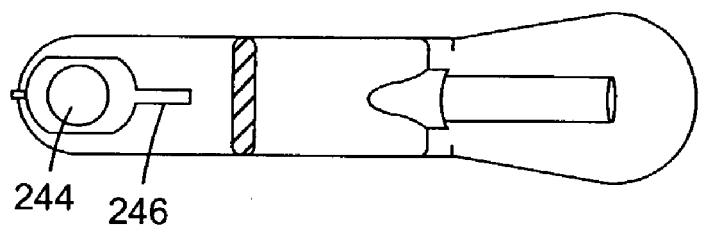
FIG. 3B illustrates a sectional view of the detector taken along line A—A of FIG. 3A.
Figure 3C:
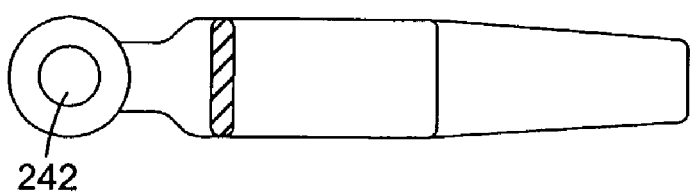
FIG. 3C illustrates a sectional view of the detector taken along line B—B of FIG. 3A.

FIGS. 2A, 2B and 2C are back, front and sectional views, respectively, of a blood sampling cuvette, and FIGS. 3A, 3B and 3C are sectional views of a sensor/detector for use with this cuvette. In the embodiment shown, the shapes of the cuvette and the sensor/detector are configured so that they positively lock together; however, other configurations can be used so long as the position of the sensor/detector is fixed with respect to the cuvette.

The cuvette preferably is disposable and comprises molded polycarbonate components that can be bonded together to form a leak-free cuvette, for example, by ultrasonic welding. Cuvette 200 has chamber 203 with inlet port 202 and outlet port 204 and is assembled from housing 208 which may comprise a unitary piece or multiple components. The inlet and outlet ports are preferably twist lock connectors. Within chamber 203 are mixing posts 205 which serve to mix the blood as it enters the chamber. Each housing has window 210 that is sufficiently transparent to permit the passage of the desired wavelength of light through the cuvette chamber. Windows 210 is sealed to housing 208 to prevent any leakage of fluid. The blood flow pathway of the chamber is typically narrower than the pathway leading into the chamber, and a typical chamber thickness for a cuvette useful in the practice of this invention is about 0.08 inches (about 0.20 cm). Housing 208 is provided with alignment slots 207 that engage with an alignment ridge on the sensor/detector. A preferred cuvette for use in sampling the blood is described in U.S. Pat. Nos. 5,456,253 and 5,499,627 (Steuer et al.), hereby incorporated herein by reference.

The processed blood is sampled at a fixed rate, e.g., every 100 milliseconds (msecs), via the use of transmittance light spectroscopy, as it passes through chamber 203 in the cuvette. The light sources and receivers are contained within a hardware sensor/detector 240 that attaches to the user interface/control module 190 by line 195. User interface/control module 190 also permits the display of hematocrit data.

The sensor/detector apparatus 240 is shown in FIGS. 3A, 3B and 3C, which are side and sectional views of the sensor/detector. Sensor/detector 240 permits detection of radiation passing through cuvette chamber 203 and the processed blood therein. The sensor/detector is housed in a molded clamp and connected electronically to control module 190. Sensor/detector 240 comprises sets of light emitting diodes (LEDs), i.e., photoemitter 242, that emits light in the appropriate wavelengths through the blood in the measurement window of the cuvette. The absorption of light is measured by one or more detectors 244 configured to receive the light passing through the window. Specific wavelengths of light transmitted through blood are affected by the concentration of oxygen, water, and red blood cells. Thus the associated electronic circuitry and software linked to the detector are capable of detecting red blood cell concentration, accounting for absorption and scattering characteristics, and supplying a hematocrit value. The transmitted values are used to calculate a hematocrit value of the sample. Those of skill in the art will recognize that the LEDs are selected to emit light in wavelengths appropriate for the geometry of the system and the algorithms used to calculate blood component characteristics. For example, in the present system the ratio of two wavelengths may be used to measure the hematocrit of the blood, i.e., 830 nm/1305 nm. The 830 nm (nanometer) wavelength is not extinguished by non-hemoglobin components of the blood while the 1305 nm wavelength is. Oxygen saturation is similarly measured by the ratio of two wavelengths, i.e., 660 nm/830 nm. Because the wavelengths are not at the ideal isobestic point for hemoglobin, the saturation value may be used to make a slight correction to the hematocrit measurement.

Multiple hematocrit readings are taken each second during the process of emptying the centrifuge bowl into the transfer bag. For example, 150 samples may be measured by the system each second. Those samples may be filtered so that a sampling rate of ten (10) samples per second is used by the system to calculate hematocrit values. Those of skill in the art will appreciate, however, that other sampling rates could be selected within the scope of the present invention. These values are weighted with the blood flow rate in order to produce an average hematocrit value for that bowl's contents, the volume of which is known, or for other measured known volumes in other blood processing procedures. The term "known volume" as used herein can be determined through knowledge of the containment bowl size in batch processing operations using a centrifuge bowl. Alternatively, this volume can be determined through the knowledge of the blood flow through the outlet of the system via measurement (e.g. a flow probe), or through knowledge of the pump rate and pump volume displacement and a detection mechanism capable of determining that fluid is present in the outlet. These alternative known volume derivations are applicable to both batch processing applications as well as to continuous processing methods. Sensor/Detector 240 is designed to clip onto cuvette 200. Sensor/Detector 240 is also provided with an alignment ridge 246 that engages alignment slots 207 on the cuvette. Engagement is accomplished by squeezing arms 248 towards each other to spread photoemitter 242 and detector 244 so that the sensor/detector 240 can be clipped onto the cuvettes. The proper alignment of cuvette and detector assists in providing a firm fit.

Data Correction Algorithms

During operation of the hematocrit sensing circuit during bowl evacuation hematocrit readings or sample data can be lost for two reasons. First, during start-up, there is air in the line. The measurement circuitry has a response time when converting from air signals to known blood hematocrit values, referred to as a lock time. The lock time is a function of the circuit components and may be, for example, 0.6 seconds. The second reason is due to the presence of air bubbles or other non-blood substances that interfere with the signal.

Figure 4:
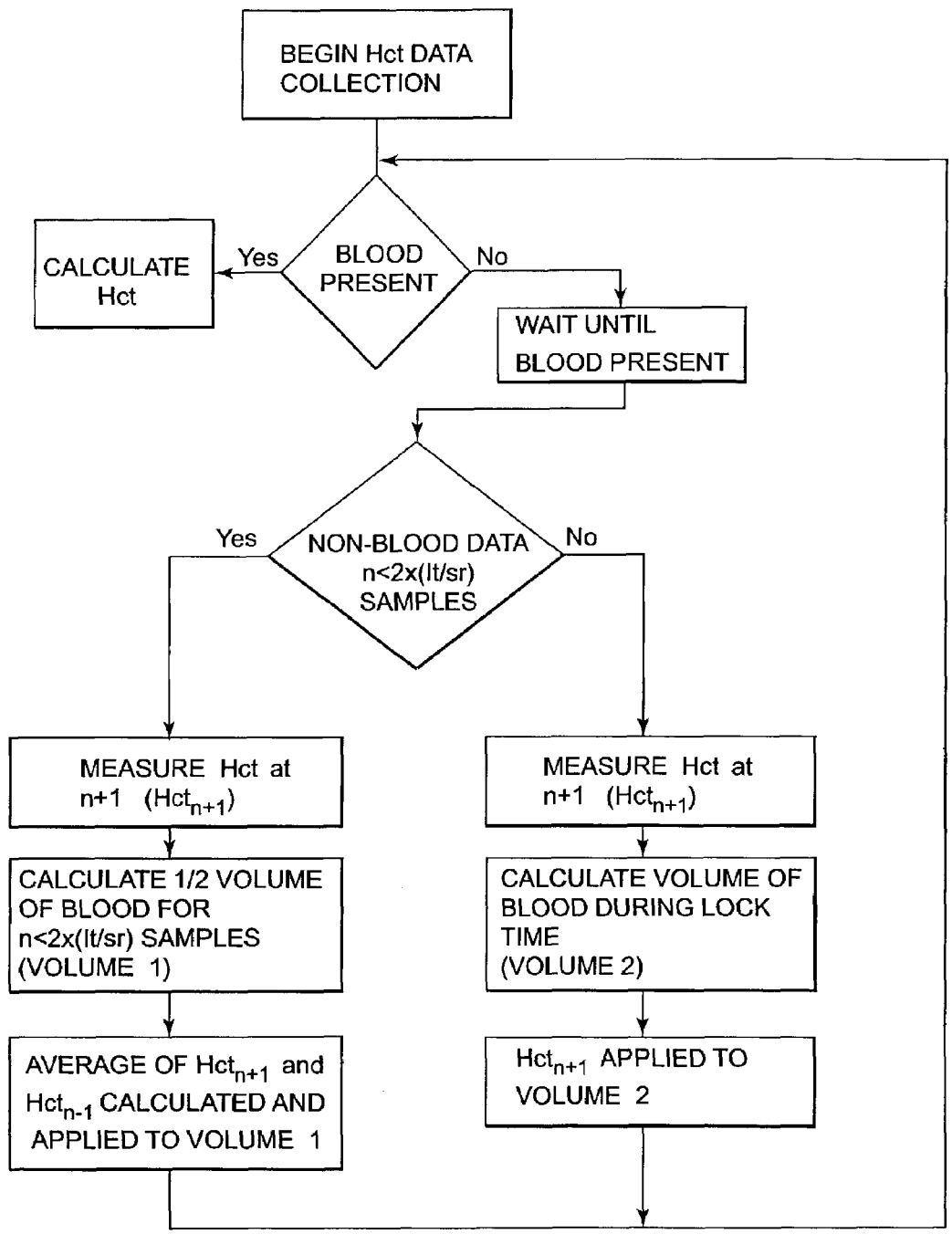
FIG. 4 is a flow chart illustrating the steps carried out during the preferred method of the invention to obtain an accurate hematocrit value of processed or separated blood.

In order to correct for this loss of sample data, the hematocrit sensing circuit uses a first algorithm to correct for the lock time, and a second algorithm to account for the interference from air bubbles or other non-blood substances. A flow chart illustrating these algorithms is shown in FIG. 4.

1. Loss of Sample Data During Start-Up.

During start-up, the lock time, or response time of the circuitry can cause samples to be lost. The blood volume lost is a function of the lock time, sampling rate and flow rate. For example, for a lock time of 0.6 seconds and a sampling rate of 10 samples per second 6 samples will be lost representing from 1 to 13 milliliters (ml) at flow rates from 100 to 1300 ml/min. If these lost samples are not accounted for, the minimum sampling volume for the bowl (described in more detail hereafter) may not be achieved. This results in the system being unable to provide an accurate hematocrit value for the bowl being evacuated. The start-up algorithm allows some of this lost sample data to be recaptured. The algorithm works as follows. When a good hematocrit sample value (i.e. non-air) $Hct_{n+1}$ is obtained after a number of non-blood samples at least as great as 2 multiplied by the lock time/sampling rate (i.e., n<(2× lock time/sample rate) the milliliters (ml) pumped during the lock time prior to the good sample is calculated (volume 2). (In FIG. 4, lock time divided by sampling rate is abbreviated (1t/sr)). This calculation may be based on measured flow rate, pump speed or by other means known to those of skill in the art. The value of the good hematocrit sample ($Hct_{n+1}$) is then assigned to the milliliters pumped during the lock time (volume 2). As an alternative to assigning the value of the good hematocrit sample ($Hct_{n+1}$) to the milliliters pumped during the lock time additional good hematocrit samples ($Hct_{n+1} \ldots _{n+x}$) could be measured to determine a slope. This slope could then be extrapolated backwards to determine values for the lost samples.

2. Loss of Samples Due to Air Bubble During Bowl Evacuation.

During evacuation of processed blood from the bowl it is possible for non-blood substances such as air bubbles to be present in the recovered blood. For small bubbles or obstructions which pass through the cuvette in less than twice the lock time the loss of approximately the same amount of samples of blood in milliliters as the size of the air bubble in milliliters is caused. The air bubble correction algorithm allows these lost sample data to be recaptured. The air bubble algorithm works as follows. When a good hematocrit ($Hct_{n+1}$) sample value is obtained after a number of non-blood samples less than 2× lock time/sampling rate (n<2× lock time/sampling rate) have been obtained, one-half (½) the milliliters pumped during those non-blood samples is calculated (volume 1). The average of the good hematocrit value ($Hct_{n+1}$) and the previous good hematocrit value obtained just prior to the non-blood samples ($Hct_{n-1}$) is calculated. That average hematocrit value is expressed by the following equation:

$$\frac{(Hct_{n+1}) + (Hct_{n-1})}{2}$$

This average value is then assigned to one-half (½) of the calculated value of milliliters pumped during the non-blood samples (volume 1). Alternatively, additional pre-bubble hematocrit samples and additional post-bubble hematocrit samples could be measured and used to formulate an equation for that segment of blood data. Instead of allocating a simple average to the missing samples, the equation could be used to calculate the values for those samples.

Determination of Minimum Volume for Hematocrit Measurement of Containment Bowl

Figure 5:
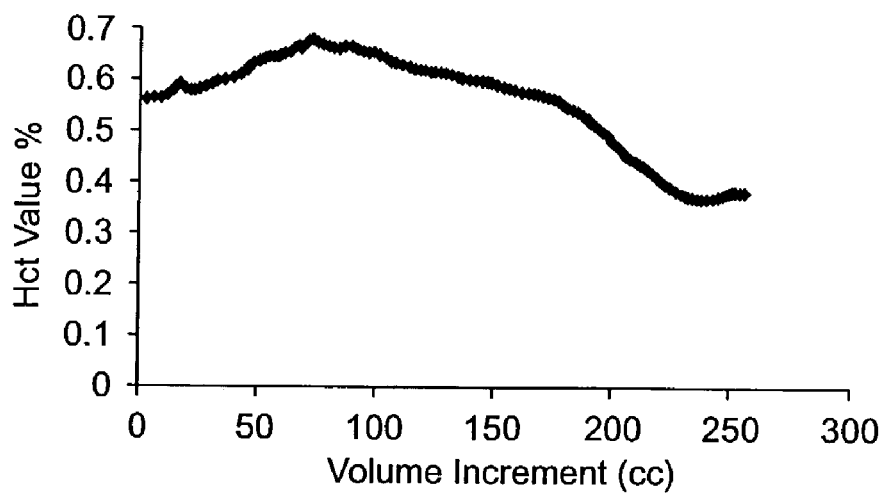
FIG. 5 is a graph of hematocrit (Hct) measured versus the volume of processed blood displaced from the containment bowl.

During blood processing procedures it is desirable to be able to measure and assign a hematocrit value for each containment bowl processed. FIG. 5 is a sample graph of hematocrit (Hct) measured versus the volume increment of processed blood displaced from the containment bowl. Based on FIG. 5 it is clear the hematocrit value of processed blood is not constant during an empty cycle but will vary depending on the volume of blood displaced. Because of this variation of values it has been found that in order to obtain an accurate average value of hematocrit for blood processed in a given containment bowl it is necessary to obtain samples of hematocrit from at least a minimum volume of processed blood evacuated from the containment bowl. The minimum volume differs depending on bowl size and the type of procedure being performed. Additionally, it will be appreciated by those of skill in the art that the measured volume of contents emptied from a containment bowl will differ from the stated size of the bowl depending on the type of procedure being performed. For example, for a bowl size of 135 ml the minimum volume which must be sampled for an accurate average hematocrit value for the bowl has been empirically determined to be 95 ml for an autologous blood salvage (ABS) procedure and 143 ml for a plasma sequestration (PRP) procedure. For a bowl size of 250 ml the minimum volumes are 217 ml for an autologous blood salvage procedure and 219 ml for a plasma sequestration procedure. If insufficient sample data has been collected during bowl evacuation (i.e. hematocrit samples from less than the minimum volume) no bowl hematocrit value will be reported.

To determine the minimum volume of blood which must be sampled in order to obtain an accurate average hematocrit reading for each of the four conditions set forth above (250 ml bowl/ABS; 250 ml bowl/PRP; 135 ml bowl/ABS; 135 ml bowl/PRP), human blood was processed under worst case conditions and outlet hematocrit sample values were obtained during the empty cycle. A minimum of four processing cycles per condition were performed.

Figure 6:
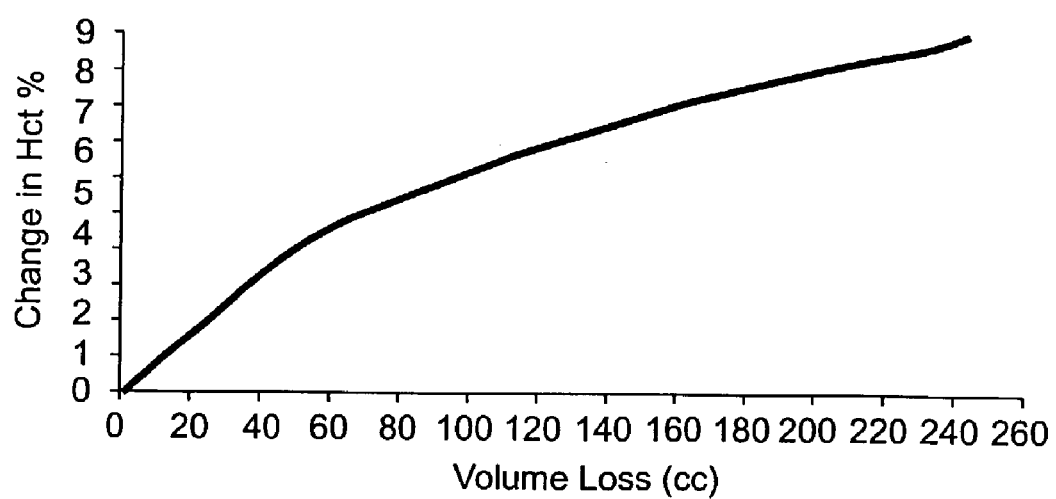
FIG. 6 is a graph showing the change in final Hct value as a function of removing Hct sample data.

The data collected was analyzed in the following manner. The algorithm used to account for volume loss due to air bubbles or other obstructions in the blood passing through the measurement cuvette was applied to the data. Next, the outlet hematocrit values tagged with the volume data position were sorted from lowest hematocrit value to highest hematocrit value. The final hematocrit value for the total volume measured was then calculated, taking into account all measured data points. Then data points were removed from the final calculated hematocrit value, one data point at a time, starting with the lowest hematocrit value and then the final hematocrit value was recalculated. Lowest hematocrit values were subtracted first from the calculated hematocrit value because they produced the biggest mean shift and therefore represent the worst case scenario. Next the initial calculated hematocrit value was then compared to the recalculated value to determine how much of an hematocrit value shift occurred. A graph showing the change in the final hematocrit value versus the volume loss is set forth in FIG. 6. FIG. 6 is a graph for a 250 ml bowl/ABS procedure. Similar graphs for the other conditions are not set forth.

From each of the processing runs a volume loss value was obtained which produced a 1.5% hematocrit shift. For each condition an average volume loss value (1.5 Hct loss (cc)) was calculated for the 1.5% hematocrit shift. Although a 1.5% hematocrit shift was selected for these calculations it should be appreciated that other hematocrit shift percentages could be selected depending on the accuracy desired. Known average volume and standard deviation (sd) values for these bowl sizes and procedures were used, along with the average volume loss information to calculate the final minimum volume limits. Examples of the data obtained and analyzed with respect to these four processing conditions is set forth below.

Avg Vol = 139.93 cc, sd = 6.952    135 ml bowl/ABS
(Final minimum volume) = 139.93 cc − (3 × 6.952 cc) − 24.2 cc = 94.88 cc)

| RUN # | Raw volume measured (cc) | Corrected volume (cc) | 1.5 Hct loss (cc) |
|---|---|---|---|
| 1 | 135 | 144 | 19 |
| 2 | 127 | 145 | 19 |
| 3 | 115 | 143 | 28 |
| 4 | 117 | 145 | 27 |
| 5 | 129 | 145 | 28 |
|   |     |     | 24.2 |

Avg Vol = 167.8 cc, sd = 5.42    135 ml bowl/PRP
(Final minimum volume) = 167.8 cc − (3 × 5.42 cc) − 8.25 cc = 143.29 cc)

| RUN # | Raw volume measured (cc) | Corrected volume (cc) | 1.5 Hct loss (cc) |
|---|---|---|---|
| 1 | 148 | 163 | 8 |
| 2 | 161 | 173 | 8 |
| 3 | 158 | 176.5 | 9 |
| 4 | 159 | 172 | 8 |
|   |     |     | 8.25 |

Avg Vol = 245.97 cc, sd 2.943    250 bowl/ABS
(Final minimum volume) = 245.97 cc − (3 × 2.943 cc) − 20.2 cc = 216.94 cc)

| RUN # | Raw volume measured (cc) | Corrected volume (cc) | 1.5 Hct loss (cc) |
|---|---|---|---|
| 1 | 135 | 144 | 19 |
| 2 | 227 | 247 | 21 |
| 3 | 240 | 252 | 20 |
| 4 | 241 | 248 | 19 |
| 5 | 243 | 249 | 20 |
|   |     |     | 20.2 |

Avg Vol = 256.5 cc, sd = 8.22    250 bowl/PRP
(Final minimum volume) = 256.5 cc − (3 × 8.22 cc) − 12.8 cc = 219.04 cc)

| RUN # | Raw volume measured (cc) | Corrected volume (cc) | 1.5 Hct loss (cc) |
|---|---|---|---|
| 1 | 216 | 240 | 10 |
| 2 | 212 | 260 | 16 |
| 3 | 239 | 245 | 13 |
| 4 | 237 | 242.5 | 11 |
| 5 | 227 | 244 | 14 |
|   |     |     | 12.8 |

Automatic Start

This feature couples the use of the hematocrit detector with an initializing sequence. Before the equipment is used in a blood recovery system, the hematocrit sampling system is verified for accuracy prior to initiation of the measurement process. A verification process utilizing the verification filter compares the percent transmittance value of the system at start-up with calibration values stored in memory. The values stored in memory are the original calibration data performed with the same verification filter at the time the device was manufactured. This comparison validates the accuracy of the system. If the compared values are not within an acceptable range the hematocrit sampling circuit is disabled and/or a warning is provided to the operator.

Sensor/detector 240 is stored upon verification filter 250 by clipping the detector onto the filter. The filter has a surface contour which mates with sensor/detector 240 in a manner similar to the cuvette. During storage, the sensor/detector measures the transmittance value of the filter media in the verification filter. In order to start the hematocrit sampling system, an operator must remove the sensor/detector from the verification filter and place it on the blood sampling cuvette. The removal of the detector causes a change in the light transmittance values collected by the detector. The blood salvage system controller is programmed to sense this change and automatically turn the hematocrit system on. No operator intervention is needed. Therefore, as soon as the sensor/detector is clipped to the cuvette it is armed to sample hematocrit. Alternatively, the sensor/detector could be configured so that the hematocrit system is automatically turned on at the time the sensor/detector is clipped to the cuvette. This feature reduces the risk that hematocrit sampling data will be lost due to operator error.

Although particular embodiments have been disclosed herein in detail, this has been done for purposes of illustration only, and is not intended to be limiting with respect to the scope of the appended claims, which follow. In particular, it is contemplated by the inventor that various substitutions, alterations, and modifications may be made to the invention without departing from the spirit and scope of the invention as defined by the claims.

What is claimed is:

1. A method of determining the average hematocrit of blood processed in a blood processing system, comprising:
   providing a blood processing system having a blood inlet and a blood outlet, the blood processing system being sized to process a known volume of blood during a processing cycle;
   providing a hematocrit measurement circuit connected to measure the hematocrit of blood flowing through the outlet of the blood processing system, the hematocrit measurement circuit having a display for reporting hematocrit values;
   determining a minimum volume of the known volume of blood which must be measured for hematocrit in order for an average hematocrit value for the known volume of blood to be calculated within a predetermined degree of accuracy;
   evacuating processed blood from the system through the blood outlet;
   making a plurality of hematocrit measurements of the processed blood;
   calculating from the plurality of hematocrit measurements an average hematocrit value for a first volume of processed blood; and
   comparing the first volume to the minimum volume.

2. The method of claim 1 further comprising reporting the average hematocrit of the known volume of processed blood if the first volume is at least as great as the minimum volume.

3. A method of measuring hematocrit in processed blood comprising:
   providing a blood processing system having a blood inlet and a blood outlet, the blood processing system being sized to process a known volume of blood during each processing cycle;
   providing a hematocrit measurement circuit having a hematocrit sensor connected to measure the hematocrit of blood flowing through the outlet of the blood processing system, the hematocrit measurement circuit having a known lock time after which the circuit first responds to the presence of blood sensed by the sensor;
   evacuating processed blood from the system through the blood outlet;
   making a plurality of hematocrit measurements of the processed blood;
   assigning a hematocrit value to a first volume of processed blood passing the hematocrit sensor during the lock time; and
   calculating from the plurality of hematocrit measurements and assigned hematocrit value an average hematocrit value of the known volume of processed blood evacuated from the system.

4. The method of claim 3 further including determining the presence of non-blood substances in the processed blood from the plurality of hematocrit measurements and assigning a hematocrit value to a second volume of processed blood, the second volume being determined from hematocrit measurements of non-blood substances in the processed blood.

5. The method of claim 4 wherein the step of assigning a hematocrit value to the second volume of processed blood comprises using an algorithm that calculates the hematocrit value based on at least one of the plurality of hematocrit measurements.

6. The method of claim 5 wherein the step of using an algorithm to calculate a hematocrit value for the second volume of processed blood comprises assigning to the second volume of processed blood a hematocrit value equal to the average of the last processed blood hematocrit measurement prior to the non-blood substance and the first processed blood hematocrit measurement after the non-blood substance.

7. The method of claim 3 wherein the assigning step comprises using an algorithm that calculates the hematocrit value based on at least one of the plurality of hematocrit measurements.

8. The method of claim 7 wherein the step of using the algorithm to calculate the hematocrit value comprises assigning to the first volume of processed blood a hematocrit value equal to the first processed blood hematocrit measurement after the lock time.

9. The method of claim 7 wherein the step of using the algorithm to calculate the hematocrit value comprises determining a slope of the first N processed blood hematocrit measurements after the lock time and extrapolating backwards using the slope to assign a hematocrit value to the first volume of processed blood.

10. A method of measuring hematocrit in processed blood comprising:
    providing a blood processing system having a blood inlet and a blood outlet;
    providing a hematocrit measurement circuit connected to measure the hematocrit of blood flowing through the outlet of the blood processing system;
    evacuating processed blood from the system through the blood outlet;
    making a plurality of hematocrit measurements;
    determining the presence of non-blood substances in the processed blood from the hematocrit measurements;
    assigning a hematocrit value to a first volume of processed blood based on hematocrit measurements of non-blood substances in the processed blood; and
    calculating from the measured hematocrit and assigned hematocrit values an average hematocrit value of process blood evacuated from the system;
    wherein the hematocrit measurement circuit includes a hematocrit sensor connected to measure the hematocrit of blood flowing through the outlet of the blood processing system and wherein the hematocrit measurement system has a known lock time after which the circuit first resnonds to the presence of blood sensed by the sensor, the method including assigning a hematocrit value to a second volume of recessed blood passing the hematocrit sensor during the lock time.

11. The method of claim 10 wherein the step of assigning a hematocrit value to the second volume of processed blood comprises using an algorithm that calculates the hematocrit value based on the measured hematocrit.

12. The method of claim 11 wherein the step of using the algorithm to calculate the hematocrit value comprises assigning to the second volume of processed blood a hematocrit value equal to the first processed blood hematocrit measurement after the lock time.

13. The method of claim 10 wherein the step of assigning a hematocrit value to the first volume of processed blood comprises using an algorithm that calculates the hematocrit value based on at least one of the hematocrit measurements.

14. The method of claim 10 wherein the step of using the algorithm to calculate the hematocrit value comprises assigning to the first volume of processed blood a hematocrit value equal to the average of the last processed blood hematocrit measurement prior to the non-blood substance and the first processed blood hematocrit measurement after the non-blood substance.

* * * * *